(12) United States Patent
Patten et al.

(10) Patent No.: US 7,716,995 B2
(45) Date of Patent: May 18, 2010

(54) CORIOLIS FLOW METER AND METHOD FOR DETERMINING FLOW CHARACTERISTICS

(75) Inventors: Andrew T. Patten, Boulder, CO (US); Graeme Ralph Duffill, Boulder, CO (US); Denis M. Henrot, Louisville, CO (US)

(73) Assignee: Micro Motion, Inc., Boulder, CO (US)

( * ) Notice: Subject to any disclaimer, the term of this patent is extended or adjusted under 35 U.S.C. 154(b) by 295 days.

(21) Appl. No.: 11/908,385

(22) PCT Filed: Mar. 29, 2005

(86) PCT No.: PCT/US2005/010367
§ 371 (c)(1),
(2), (4) Date: Sep. 11, 2007

(87) PCT Pub. No.: WO2006/104485
PCT Pub. Date: Oct. 5, 2006

(65) Prior Publication Data
US 2008/0184813 A1    Aug. 7, 2008

(51) Int. Cl.
*G01F 1/84* (2006.01)
(52) U.S. Cl. .................................. 73/861.355
(58) Field of Classification Search ...............................
73/861.355–861.357
See application file for complete search history.

(56) References Cited

U.S. PATENT DOCUMENTS

| | | | |
|---|---|---|---|
| 4,331,025 A | 5/1982 | Ord, Jr. | |
| 4,524,610 A | 6/1985 | Fitzgerald et al. | |
| 4,930,351 A * | 6/1990 | Macy et al. | 73/504.04 |
| 5,069,074 A * | 12/1991 | Young et al. | 73/861.356 |
| 5,253,533 A | 10/1993 | Lam et al. | |
| 5,285,686 A * | 2/1994 | Peters | 73/504.15 |
| 5,359,881 A | 11/1994 | Kalotay et al. | |
| 5,576,500 A | 11/1996 | Cage et al. | |
| 5,661,232 A | 8/1997 | Van Cleve et al. | |
| 5,734,112 A | 3/1998 | Bose et al. | |

(Continued)

FOREIGN PATENT DOCUMENTS

DE    10235322 A1    2/2004

(Continued)

*Primary Examiner*—Jewel Thompson
(74) *Attorney, Agent, or Firm*—The Ollila Law Group LLC

(57) ABSTRACT

A Coriolis flow meter (5) is provided according to an embodiment of the invention. The meter (5) includes one or more flow conduits (103), at least two pickoff sensors (105, 105') affixed to the one or more flow conduits (103), a driver (104) configured to vibrate the one or more flow conduits (103), and meter electronics (20) coupled to the at least two pickoff sensors (105, 105') and to the driver (104). The meter electronics (20) vibrate the one or more flow conduits (103) of the flow meter (5) with a first vibration frequency and in a first out-of-phase bending mode, measure a first vibrational response, with the first vibrational response being generated in response to the first vibration frequency, vibrate the one or more flow conduits (103) with at least a second vibration frequency and in the first out-of-phase bending mode, measure a second vibrational response, and determine at least a mass flow rate and a viscosity using the first and second vibrational responses.

37 Claims, 5 Drawing Sheets

U.S. PATENT DOCUMENTS

| | | |
|---|---|---|
| 5,861,561 A | 1/1999 | Van Cleve et al. |
| 5,877,409 A | 3/1999 | Girling |
| 5,929,344 A | 7/1999 | Hays et al. |
| 6,006,609 A | 12/1999 | Drahm et al. |
| 6,092,429 A | 7/2000 | Cunningham et al. |
| 6,347,293 B1 | 2/2002 | Cunningham et al. |
| 6,502,466 B1 | 1/2003 | Cage et al. |
| 6,651,513 B2 | 11/2003 | Wenger et al. |
| 2008/0184813 A1 * | 8/2008 | Patten et al. ........... 73/861.355 |

FOREIGN PATENT DOCUMENTS

| | | |
|---|---|---|
| RU | 2000104841 A | 2/2002 |

* cited by examiner

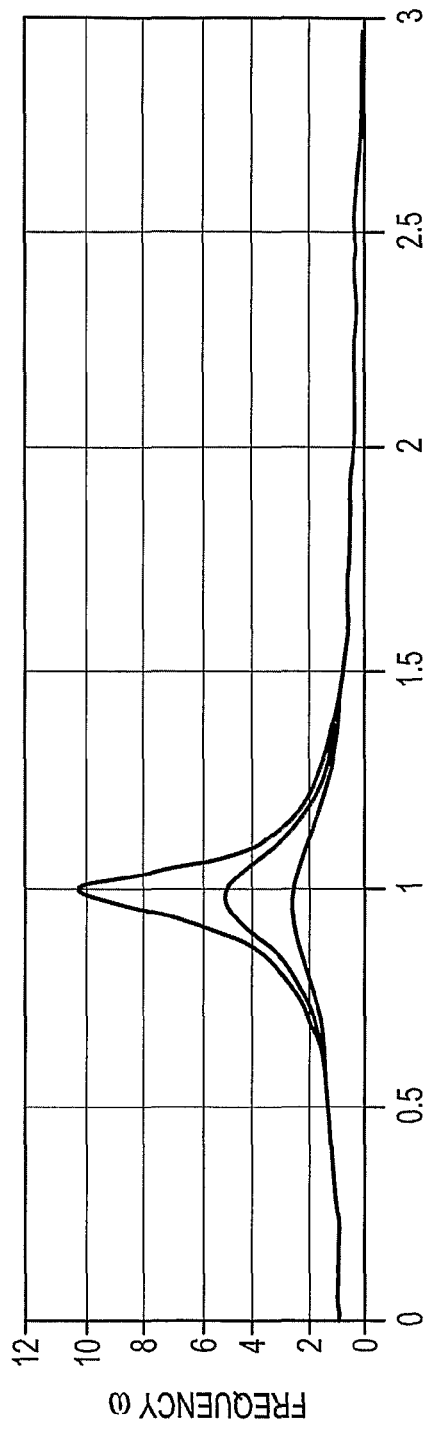
FIG.4A MAGNITUDE
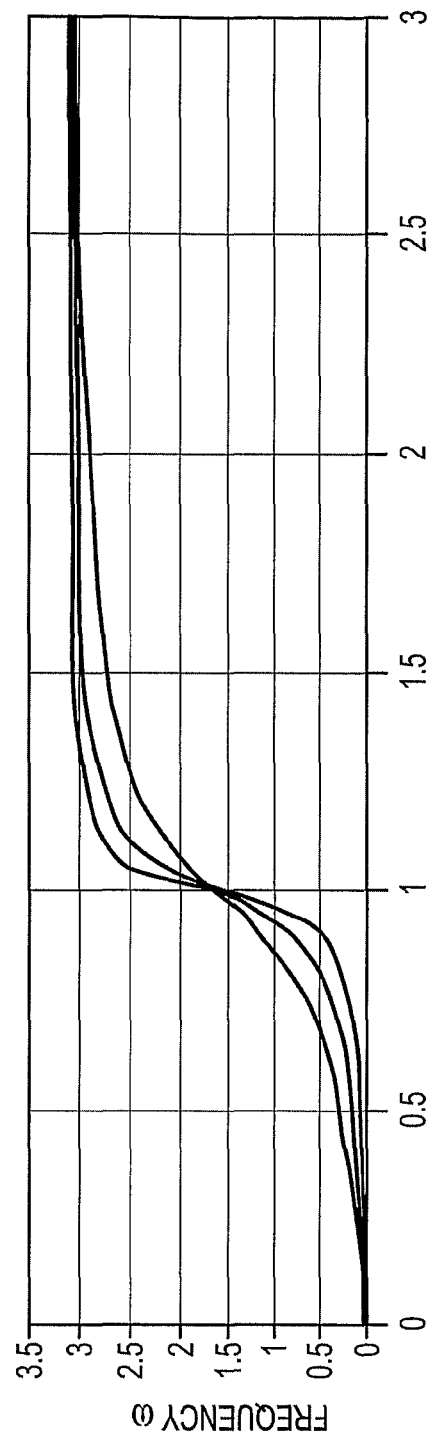
FIG.4B PHASE

CORIOLIS FLOW METER AND METHOD FOR DETERMINING FLOW CHARACTERISTICS

BACKGROUND OF THE INVENTION

1. Field of the Invention

The present invention relates to a Coriolis flow meter and method for determining flow characteristics, and more particularly, to a Coriolis flow meter and method for determining flow characteristics using two or more vibrational responses.

2. Statement of the Problem

Vibrating conduit sensors, such as Coriolis mass flow meters, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness and damping characteristics of the containing conduit and the material contained therein.

A typical Coriolis mass flow meter includes one or more conduits that are connected inline in a pipeline or other transport system and convey material, e.g., fluids, slurries and the like, in the system. Each conduit may be viewed as having a set of natural vibration modes including, for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pickoff sensors) are typically employed in order to measure a vibrational response of the flow conduit or conduits, and are typically located at positions upstream and downstream of the actuator. The two pickoff sensors are connected to electronic instrumentation by cabling, such as two independent pairs of wires. The instrumentation receives signals from the two pickoff sensors and processes the signals in order to derive a mass flow rate measurement.

Traditional Coriolis mass flow meters provide continuous measurement of the mass flow rate, density, and temperature of the flow medium flowing through the flow meter. However, a change in any of the flow characteristics of the flow medium can cause an increase or decrease in the mass loading on the flow meter, and hence will cause an error in the indicated density, among other things.

Designers of vibrating element transducers, such as Coriolis mass flow meters or densitometers, generally try to maximize the sensitivity of the mass, density, and temperature while minimizing the transducer sensitivity to the viscosity, VOS, shear rate, pressure, and Reynolds number. As a result, a typical prior art flow meter is capable of accurately measuring the mass, density, and temperature but is not capable of accurately measuring additional flow characteristics such as one or more of the viscosity, VOS, shear rate, pressure, and Reynolds number. There is a need in flow meter applications to measure other flow characteristics in addition to mass, density, and temperature.

SUMMARY OF THE SOLUTION

The present invention helps solve the problems associated with determining flow characteristics of a flow meter.

A Coriolis flow meter is provided according to an embodiment of the invention. The Coriolis flow meter comprises one or more flow conduits, at least two pickoff sensors affixed to the one or more flow conduits, a driver configured to vibrate the one or more flow conduits, and meter electronics coupled to the at least two pickoff sensors and to the driver. The meter electronics is configured to vibrate the one or more flow conduits of the flow meter with a first vibration frequency and in a first out-of-phase bending mode, measure a first vibrational responsive the one or more flow conduits, with the first vibrational response being generated in response to the first vibration frequency, vibrate the one or more flow conduits with at least a second vibration frequency and in the first out-of-phase bending mode, measure a second vibrational response, with the second vibrational response being generated in response to the second vibration frequency, and determine at least a mass flow rate and a viscosity using the first vibrational response and the second vibrational response.

A method for determining flow characteristics in a Coriolis flow meter is provided according to an embodiment of the invention. The method comprises vibrating one or more flow conduits of the flow meter with a first vibration frequency and in a first out-of-phase bending mode and measuring a first vibrational response of the one or more flow conduits. The first vibrational response is generated in response to the first vibration frequency. The method further comprises vibrating the one or more flow conduits with at least a second vibration frequency and in the first out-of-phase bending mode and measuring a second vibrational response. The second vibrational response is generated in response to the second vibration frequency. The method further comprises determining at least a mass flow rate and a viscosity of the flow medium using the first vibrational response and the second vibrational response.

A Coriolis flow meter software product for determining flow characteristics in a Coriolis flow meter is provided according to an embodiment of the invention. The software product comprises a control software configured to direct a processing system to vibrate one or more flow conduits of the flow meter with a first vibration frequency and in a first out-of-phase bending mode, measure a first vibrational response of the one or more flow conduits, with the first vibrational response being generated in response to the first vibration frequency, vibrate the one or more flow conduits with at least a second vibration frequency and in the first out-of-phase bending mode, measure a second vibrational response, with the second vibrational response being generated in response to the second vibration frequency, and determine at least a mass flow rate and one or more flow characteristics using the first vibrational response and the second vibrational response. The software product further comprises a storage system that stores the control software.

ASPECTS

In one aspect, the determining further comprises determining a density.

In another aspect, the determining further comprises determining a shear rate.

In yet another aspect, the determining further comprises determining a Reynolds number.

In yet another aspect, the determining further comprises determining a velocity of sound (VOS).

In yet another aspect, the determining further comprises determining a pressure.

In yet another aspect, the viscosity comprises a kinematic viscosity.

In yet another aspect, the viscosity comprises a dynamic viscosity.

In yet another aspect, the vibrating further comprises jumping between the first vibration frequency and the second vibration frequency.

In yet another aspect, the vibrating further comprises substantially simultaneously vibrating the one or more flow conduits with the first vibration frequency and the second vibration frequency.

In yet another aspect, the vibrating further comprises sweeping between the first vibration frequency and the second vibration frequency over a predetermined sweep time period.

In yet another aspect, the first vibration frequency and the second vibration frequency are substantially equally spaced above and below a fundamental frequency of the one or more flow conduits.

In yet another aspect, the one or more flow conduits comprise two substantially U-shaped flow conduits.

DESCRIPTION OF THE DRAWINGS

FIG. 4A shows magnitude response characteristics for three different values of the damping factor $\zeta$, while FIG. 4B shows the corresponding phase response characteristics.

DETAILED DESCRIPTION OF THE INVENTION

FIGS. 1-5 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
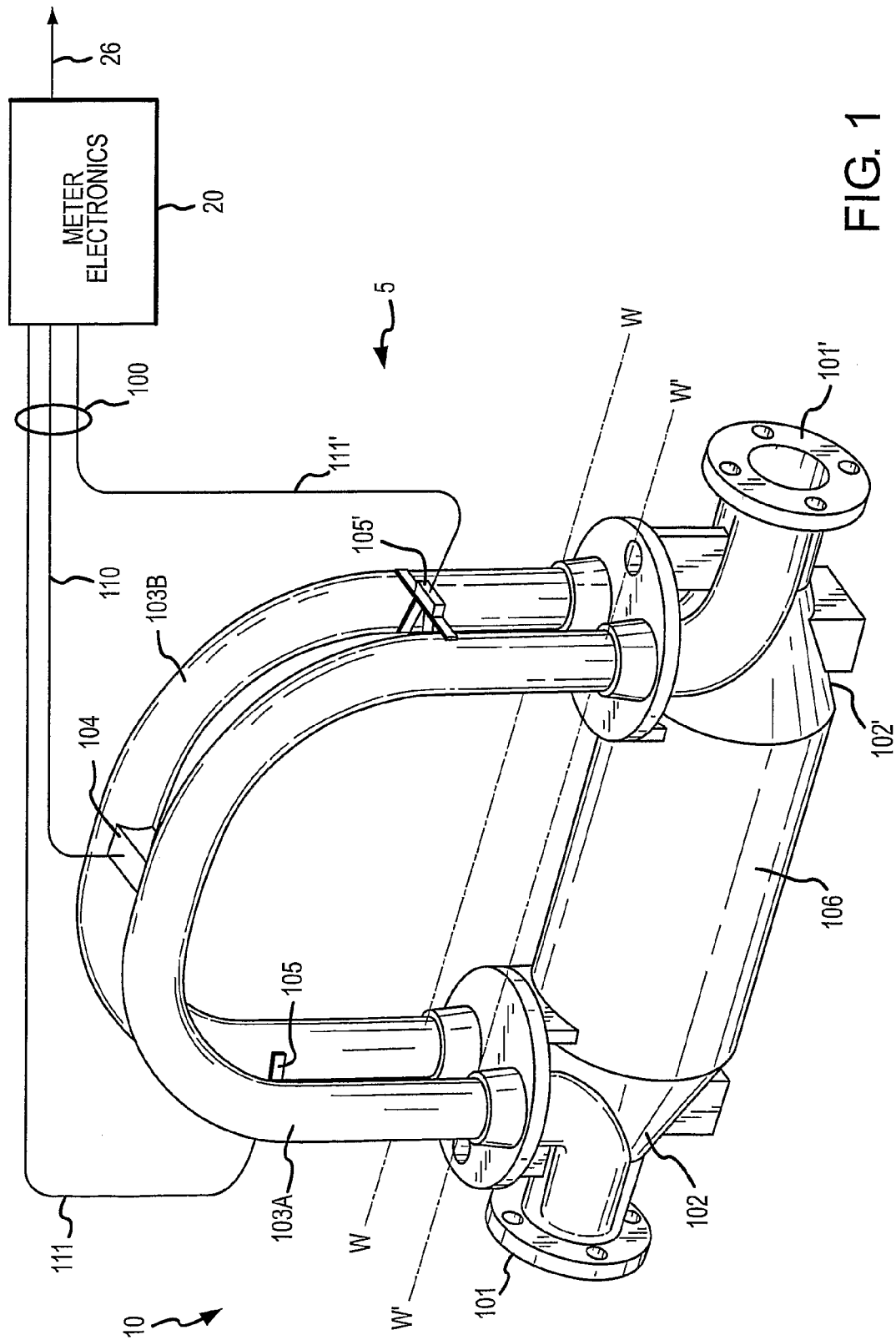
FIG. 1 illustrates a Coriolis flow meter comprising a flow meter assembly and meter electronics.

FIG. 1 illustrates a Coriolis flow meter 5 comprising a flow meter assembly 10 and meter electronics 20. Meter electronics 20 is connected to meter assembly 10 via leads 100 to provide density, mass flow rate, volume flow rate, totalized mass flow, temperature, and other information over path 26.

Flow meter assembly 10 includes a pair of flanges 101 and 101', manifolds 102 and 102', driver 104, pick-off sensors 105-105', and flow conduits 103A and 103B. Driver 104 and pick-off sensors 105 and 105' are connected to flow conduits 103A and 103B.

Flanges 101 and 101' are affixed to manifolds 102 and 102'. Manifolds 102 and 102' are affixed to opposite ends of spacer 106. Spacer 106 maintains the spacing between manifolds 102 and 102' to prevent undesired vibrations in flow conduits 103A and 103B. When flow meter assembly 10 is inserted into a pipeline system (not shown) which carries the material being measured, material enters flow meter assembly 10 through flange 101, passes through inlet manifold 102 where the total amount of material is directed to enter flow conduits 103A and 103B, flows through flow conduits 103A and 103B and back into outlet manifold 102' where it exits meter assembly 10 through flange 101'.

Flow conduits 103A and 103B are selected and appropriately mounted to inlet manifold 102 and outlet manifold 102' so as to have substantially the same mass distribution, moments of inertia, and elastic modules about bending axes W-W and W'-W' respectively. The flow conduits extend outwardly from the manifolds in an essentially parallel fashion.

Flow conduits 103A-B are driven by driver 104 in opposite directions about their respective bending axes W and W' and at what is termed the first out-of-phase bending mode of the flow meter. Driver 104 may comprise one of many well known arrangements, such as a magnet mounted to flow conduit 103A and an opposing coil mounted to flow conduit 103B. An alternating current is passed through the opposing coil to cause both conduits to oscillate. A suitable drive signal is applied by meter electronics 20, via lead 110 to driver 104.

Meter electronics 20 transmits sensor signals on leads 111 and 111', respectively. Meter electronics 20 produces a drive signal on lead 110 which causes driver 104 to oscillate flow conduits 103A and 103B. Meter electronics 20 processes left and right velocity signals from pick-off sensors 105 and 105' in order to compute a mass flow rate. Path 26 provides an input and an output means that allows meter electronics 20 to interface with an operator. The description of FIG. 1 is provided merely as an example of the operation of a Coriolis flow meter and is not intended to limit the teaching of the present invention.

Figure 2:
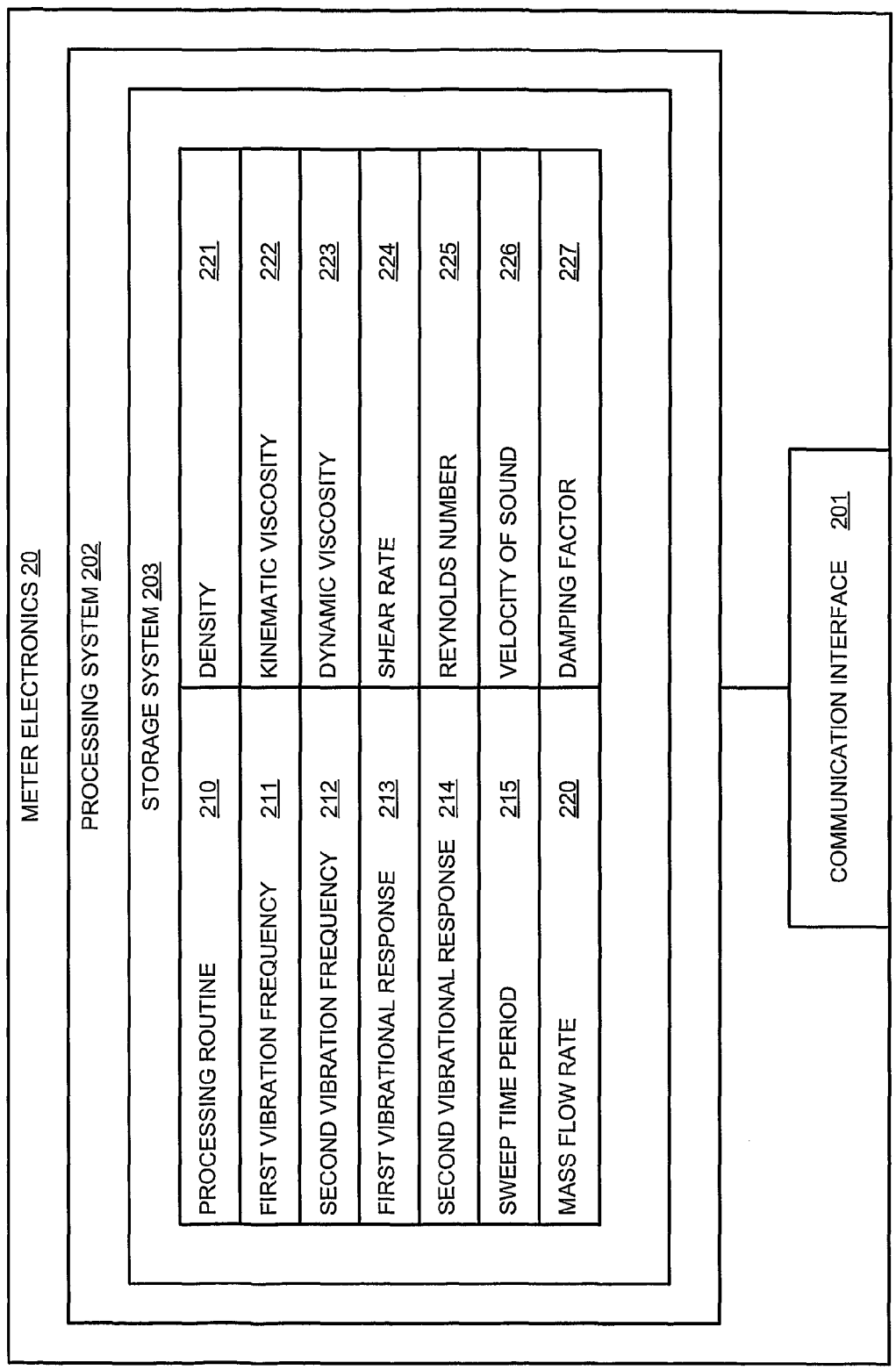
FIG. 2 shows meter electronics according to an embodiment of the invention.

FIG. 2 shows meter electronics 20 according to an embodiment of the invention. The meter electronics 20 includes a communication interface 201, a processing system 202, and a storage system 203. The processing system 202 is coupled to the communication interface 201.

The communication interface 201 enables communications between the meter electronics 20 and external devices. The communication interface 201 enables transmission of computed flow characteristics to an external device via the path 26. The external devices can include the flow meter assembly 10 (via the leads 100 of FIG. 1), a monitoring device or devices (via the path 26 of FIG. 1), or any manner of user interface or communication device. The communication interface 201 enables the receipt of flow measurements from the flow meter assembly 10 over the leads 100. The communication interface 201 can be capable of any manner of electronic, optical, or wireless communication, for example. The interface 26 can enable communication over telephone systems and/or digital data networks. Consequently, the meter electronics 20 can communicate with remote flow meters, remote processing/monitoring devices, remote memory media, and/or remote users.

The processing system 202 conducts operations of the meter electronics 20 and processes flow measurements from the flow meter assembly 10. The processing system 202 executes a processing routine 210 and processes the flow measurements in order to produce one or more flow characteristics. The processing system 202 can comprise a general purpose computer, a microprocessing system, a logic circuit, or some other general purpose or customized processing device. The processing system 202 can be distributed among multiple processing devices. The processing system 202 can include any manner of integral or independent electronic storage medium, such as the storage system 203. Alternatively, the storage system 203 can comprise an independent electronic storage medium in communication with the processing system 202.

The storage system 203 can store flow meter parameters and data, software routines, constant values, and variable values. In one embodiment, the storage system 203 includes the processing routine 210 that is executed by the processing system 202. The storage system 203 stores variables used to operate the flow meter assembly 10. The storage system 203 in one embodiment stores variables such as a first vibration frequency 211, at least a second vibration frequency 212, a first vibrational response 213, a second vibrational response 214, and a sweep time period 215.

The storage system 203 stores one or more flow characteristics obtained from the flow measurements. The storage system 203 in one embodiment stores flow characteristics such as a mass flow rate 220, a density 221, a kinematic viscosity 222, a dynamic viscosity 223, a shear rate 224, a Reynolds number 225, a velocity of sound (VOS) 226, and a damping factor (or quality factor Q) 227. It should be understood that other flow characteristics can also be determined and recorded, such as temperature and/or pressure, for example.

The mass flow rate 220 is a measurement of the mass flow through the flow meter assembly 10. The density 221 is the density of the flow material in the flow meter assembly 10.

Viscosity of a fluid can be defined as a resistance of the fluid to shear or flow, and is a measure of the adhesive/cohesive properties of the fluid. This resistance is caused by intermolecular fiction exerted when a first fluid layer attempts to slide past another fluid layer. A measurement of the viscous property of a fluid is desirable in order to properly design and operate equipment for pumping, measuring, or otherwise handling a fluid.

The kinematic viscosity 222 can be defined as a ratio of dynamic viscosity to the density. The kinematic viscosity 222 can be calculated from the dynamic viscosity 223 and the density 221. The dynamic viscosity 223 can be defined as a tangential force per unit area required to move one horizontal plane with respect to the other at a unit velocity when maintained a unit distance apart by the fluid.

The shear rate 224 can be defined as the rate of change of velocity at which one layer of fluid passes over another fluid layer.

The Reynolds number 225 can be defined as a measure of the importance of inertia to viscosity effects. At high Reynolds numbers, a flow may become turbulent, exhibiting qualitatively different behavior than the same liquid at a low Reynolds number.

The VOS 226 is the speed of sound in the flow medium. The VOS 226 can change with changes in the flow medium, can change with changes in density in the flow medium, or can change with changes in the composition of the flow medium, for example.

The damping factor 227 can be defined as a measure of how damped the vibration is by the flow medium. Alternatively, the damping factor 227 can be defined as a measure of the viscosity of the flow medium.

The processing system 202 executes the processing routine 210 in order to determine the one or more flow characteristics. The processing routine 210, when executed by the processing system 202, configures the processing system 202 to vibrate one or more flow conduits 103 of the flow meter 5 with the first vibration frequency 211, measure the first vibrational response 213 of the one or more flow conduits 103, with the first vibrational response 213 being generated in response to the first vibration frequency 211, vibrate the one or more flow conduits 103 with at least a second vibration frequency 212, measure a second vibrational response 214, with the second vibrational response 214 being generated in response to the second vibration frequency 212, and determine at least the mass flow rate 220 and a viscosity of the flow medium using the first vibrational response 213 and the second vibrational response 214 (see FIG. 3).

The first vibration frequency 211 and the second vibration frequency 212 can comprise any desired frequencies. In one embodiment, the first vibration frequency 211 and the second vibration frequency 212 are substantially equally spaced above and below a fundamental frequency of the flow meter assembly 10. However, other frequencies can be employed, depending on the flow medium and the ambient environment.

In one embodiment, the processing routine 210 can jump between the first vibration frequency 211 and the second vibration frequency 212. In an alternate embodiment, the processing routine 210 can substantially simultaneously vibrate the one or more flow conduits 103 with the first vibration frequency and the second vibration frequency. In yet another alternate embodiment, the processing routine 210 can sweep the vibration of the driver 104 between the first vibration frequency 211 and the second vibration frequency 212, wherein the actual drive frequency is stepped between the two frequencies according to the sweep time period 215.

Figure 3:
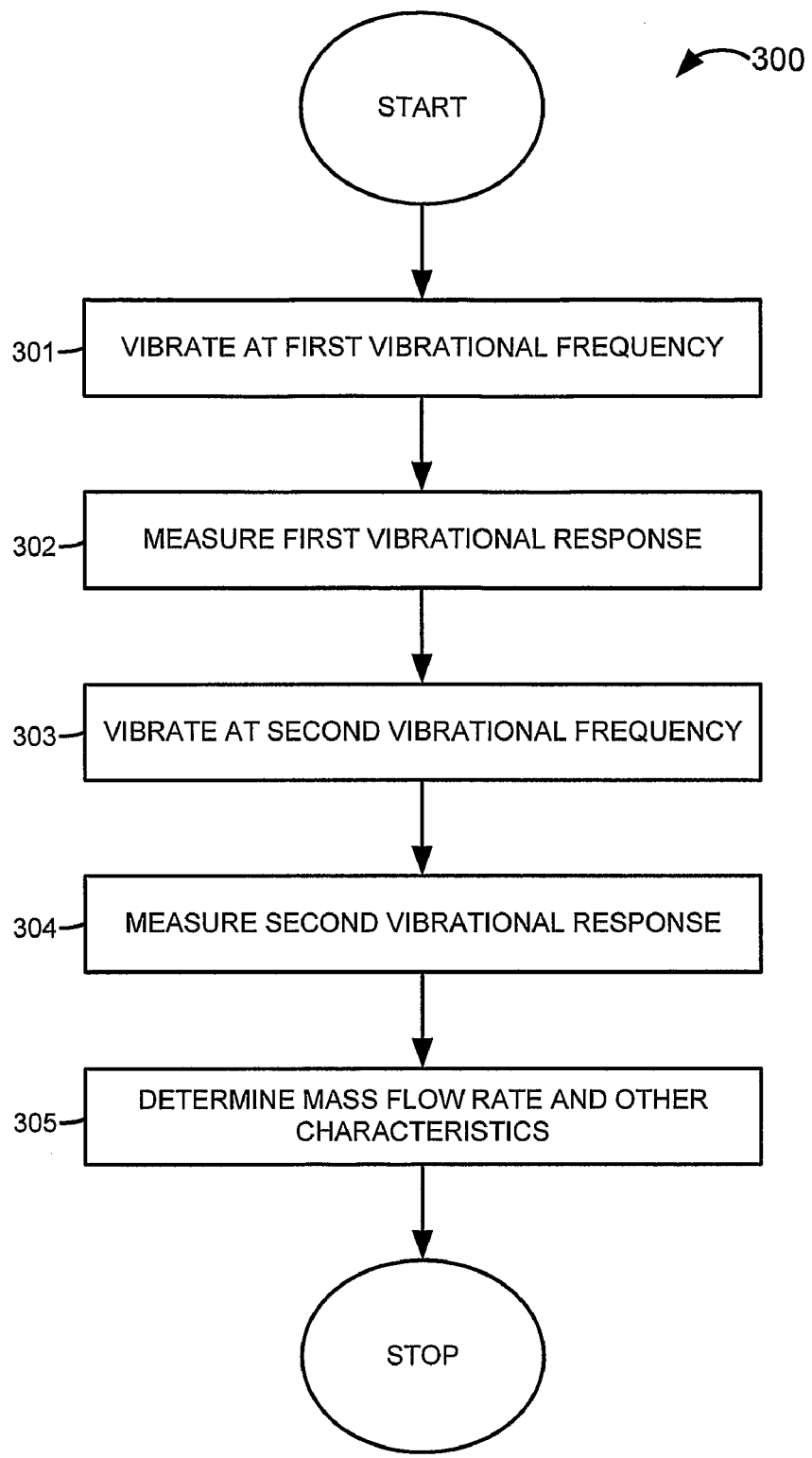
FIG. 3 is a flowchart of a method for determining flow characteristics in a Coriolis flow meter according to an embodiment of the invention.

FIG. 3 is a flowchart 300 of a method for determining flow characteristics in a Coriolis flow meter 5 according to an embodiment of the invention. In step 301, the flow tube apparatus 10 is vibrated with the first vibration frequency 211 and in a first out-of-phase bending mode by the driver 104. The first vibration frequency 211 can be a fundamental vibration frequency of the flow meter assembly 10, or can be a frequency above or below the fundamental frequency.

In step 302, the first vibrational response 213 is measured. The measurement comprises receiving signals from the pick-offs 105 and using the pick-off signals to determine the phase difference between the two pick-offs 105. The first vibrational response 213 is generated by the flow meter assembly 10 in response to the first vibration frequency 211 generated by the driver 104.

In step 303, the flow meter assembly 10 is vibrated with a second vibration frequency 212 and in the first out-of-phase bending mode by the driver 104. The second vibration frequency 212 can be any frequency that is not the first vibration frequency 211. In one embodiment, the first and second vibration frequencies 211 and 212 are substantially equally spaced above and below a fundamental frequency of the flow meter assembly 10. However, as was previously noted, the first and second vibration frequencies 211 and 212 can comprise any desired frequencies.

In step 304, a second vibrational response 214 is measured. The second vibrational response 214 is generated by the flow meter assembly 10 in response to the second vibration frequency 212 generated by the driver 104.

In step 305, the mass flow rate and other flow characteristics are determined by the meter electronics 20 from the first and second vibrational responses 213 and 214. By collecting two or more vibrational responses, the meter electronics 20 can determine many flow characteristics. The flow characteristics can include the density 221, the kinematic viscosity 222, the dynamic viscosity 223, the shear rate 224, the Reynolds number 225, the VOS 226, and the damping factor 227 of the flow material in the flow meter assembly 10.

The vibrating structure of a Coriolis flow meter 5 can be described as a single degree of freedom resonator that obeys the differential equation:

$$dx^2/dt^2 + 2\zeta dx/dt(t) + \omega_n^2 x(t) = \omega_n^2 A \cos(\omega t) \qquad (1)$$

where the right hand side represents the normalized oscillatory forcing function and $\zeta$ is the damping factor. Here, x is an instantaneous flow tube displacement and the terms dx/dt and $dx^2/dt^2$ are first and second order derivatives of the displacement, respectively.

The frequency response of this system is given by:

$$G(\omega) = 1/(1 - (\omega/\omega_n)^2 + j2\zeta\omega/\omega_n) \qquad (2)$$

with a magnitude response of:

$$|G(\omega)|^2 = 1/([1-(\omega/\omega_n)^2]^2 + (2\zeta\omega/\omega_n)2) \qquad (3)$$

and with a phase response $\phi$ of:

$$\phi(\omega) = \tan^{-1} 2\zeta\omega/\omega_n/(1-(\omega/\omega_n)^2) \qquad (4)$$

FIG. 4A shows magnitude response characteristic curves for three different values of the damping factor $\zeta$, while FIG. 4B shows the three corresponding phase response characteristic curves. The three curves reflect damping factors of $\zeta=0.05$, $\zeta=0.1$, and $\zeta=0.2$. Therefore, it can be seen from the graph that the damping factor $\zeta$ can be correlated to and derived from the phase and magnitude of the vibrational responses over at least two frequencies $\omega_1$ and $\omega_2$.

The purity of the resonator's sustained oscillation is captured in the quality factor Q, which is defined as:

$$Q = |G(\omega)|_{max} \qquad (5)$$

where the quality factor Q is equivalent to the damping factor $\zeta$.

For lightly damped systems (i.e., where $\zeta \ll 1$), it can be shown that:

$$Q \approx 1/2\zeta \approx \omega_n/(\omega_2 - \omega_1) \qquad (6)$$

where $\omega_1$ and $\omega_2$ are the half power points at which an amplitude response for the flow meter assembly 10 falls to a value of $(Q/\sqrt{(2)})$. The quantity:

$$\Delta\omega = \omega_2 - \omega_1 \qquad (7)$$

is also known as the 3 dB bandwidth of the system. Note that generally the point of maximum response $\omega_0$ is given by:

$$\omega_0 = \omega_n\sqrt{(1-2\zeta^2)} \qquad (8)$$

indicating that the maximum response $\omega_0$ occurs at a frequency lower than the undamped natural frequency $\omega_n$.

The dynamic viscosity (v) of a flow medium passing through a Coriolis mass flow meter will directly alter the structure's quality factor Q. The more viscous the flow medium, the more damped the system. Indeed, the dynamic viscosity v of the flow medium and the quality factor Q are related by:

$$Q = K_v/\sqrt{(v)} \qquad (9)$$

where $K_v$ is a proportionality constant that is divided by the square root of the viscosity v. This suggests that a method that enables the flow meter 5 to measure the system's damping factor $\zeta$ (or equivalently its quality factor Q) will yield the dynamic viscosity v, after appropriate calibration.

There are a number of methods that can be used to determine the quality factor Q. A first method measures the quality factor Q directly as defined by equation (5) by measuring the peak amplitude $|G(\omega)|_{max}$. To do this, the flow meter assembly 10 can be driven open loop through a continuum of drive frequencies encompassing $\omega_0$. This is done while maintaining the drive power constant, as a means of normalization. The difficulty with this approach is that it requires some type of absolute amplitude response calibration, which can be noisy and inaccurate and does not account for the variability of pickoff efficiency.

A second method drives the flow conduit or conduits to their nominal displacement amplitude and periodically disengages the driving force while monitoring the oscillation's amplitude decay. The time taken for the amplitude to decrease to 0.707 of its peak value will provide an alternate measure of the quality factor Q. The difficulties encountered with this method stem from the discontinuous nature of the driving function, which will instantaneously and periodically perturb the quality of the mass flow rate measurement.

A third method measures the quality factor Q of the flow meter assembly 10 by driving the flow meter assembly 10 successively at the half power points $\omega_1$ and $\omega_2$ and at the point of maximum response $\omega_0$. This is an attractive approach because the quality factor is totally dependent on the mechanical properties of the resonator, and is not dependent on the efficiency of the driver 104 or on the efficiency of the pick-offs 105. The difficulty with this approach is that when the flow meter assembly 10 is switched from one frequency to another (such as from $\omega_1$ to $\omega_0$), the flow meter assembly 10 will be disrupted and will need time to settle back into its stable regime. During this settling period, all process information (viscosity, density, and mass flow rate) can be lost or the measurement quality can be seriously degraded.

The invention provides a substantially continuous and uncompromised measurement of at least mass flow rate, density, and viscosity.

Figure 5:
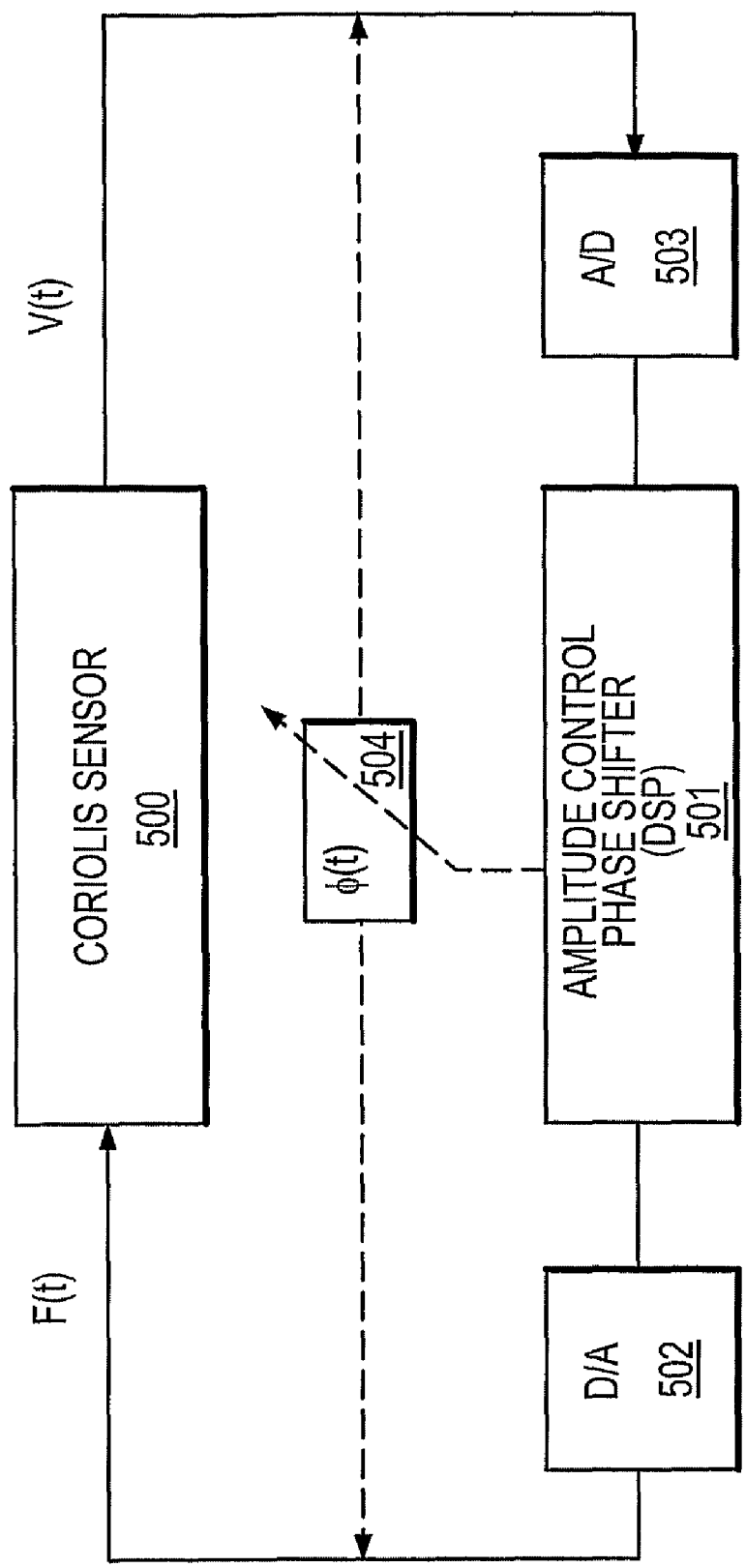
FIG. 5 shows a feedback loop for controlling a vibration frequency applied to the flow meter assembly.

FIG. 5 shows a feedback loop for controlling a vibration frequency applied to the flow meter assembly 10. The feedback loop can include the Coriolis sensor 500 (i.e., the flow meter 5), a phase shifter 501, a digital-to-analog (D/A) converter 502, an analog-to-digital (A/D) converter 503, and a phase sensor 504. In operation, the phase shifter 501 generates a digital drive signal that is converted to an analog drive signal by the D/A 502 and provided to the Coriolis sensor 500. The pickoff signal output is provided to the A/D 503, which digitized the analog pickoff signal and provides it to the phase shifter 501. The phase sensor 504 compares the input (drive) phase to the output (sensor) phase, and generates a phase difference signal to the phase shifter 501. As a result, the phase shifter 501 can control the phase shift and the frequency of the drive signal provided to the Coriolis sensor 500.

As shown in the figure, the invention controls the phase between the sensor's input and output so as to continuously cycle the closed-loop resonance between first and second vibration frequencies $\omega_1$ and $\omega_2$ while maintaining the system under closed-loop control. Such phase control can be digitally implemented using standard phase-locked loop techniques. In one embodiment, the closed-loop control can be performed by an appropriately programmed Digital Signal Processor (DSP). However, other feedback or loop control techniques can be employed and are within the scope of the description and claims.

The target phase setpoint shown in FIG. 5 is a periodic function of time such as:

$$\phi(t) = \phi_0 + \Delta\phi \sin(2\pi t/T_\phi) \qquad (10)$$

with the phase modulation index $\Delta\phi$ and the modulation period $T_\phi$ being on the order of several seconds in one embodiment. With such a slowly varying phase variation, the system closed-loop oscillating frequency will track continuously as predicted by the phase curve shown in FIG. 4B. Therefore, for every period of time $T_\phi$, all relevant variables ($\omega_0$, $\omega_1$, $\omega_2$, and mass flow rate) can be measured by tracking the relative amplitude response throughout the continuum of operating points $\omega_E[\omega_1, \omega_2]$, with no need for absolute calibration of the amplitude response.

Depending on the response time required, the density $\rho$ can be determined in various ways. For example, in one embodiment the density $\rho$ can be determined by periodically updating the density output each time the phase passes through the density calibration phase point $\rho_{cal}$. In another embodiment, the density $\rho$ is dynamically determined by applying a frequency correction factor, wherein the frequency correction factor is dependent on the actual phase and on the viscosity of the product.

The shear rate 224 can be determined by utilizing the mass flow rate 220 through the flow meter assembly 10 and from the natural resonant frequency of the flow meter assembly 10. Consequently, by changing the flow rate and/or by changing the resonant frequency of the flow meter 5 by operating in a different mode of vibration, the shear rate 224 can be modified. This capability leads to the ability to profile non-Newtonian or liquid products substantially instantaneously. Fluids for which the shearing stress is linearly related to the rate of shearing strain are designated as being Newtonian fluids. Newtonian materials are referred to as true liquids, since their viscosity or consistency is not affected by shear, such as agitation or pumping at a constant temperature. Fortunately, most common fluids, both liquids and gases, are Newtonian, including water and oils.

The Reynolds number $R_e$ 225 for the flow medium can be determined from the three prime measurements that are simultaneously measured by the flow meter assembly 10, i.e., the Reynolds number $R_e$ 225 can be determined from the mass flow rate 220, the density 221, and from the dynamic viscosity 223.

The vibrational responses generated by the Coriolis flow meter 5 can additionally be used for other purposes. For example, in one embodiment, the two or more vibrational responses can be used to determine a flexural stiffness of the flow meter assembly 10. The flexural stiffness can be used in order to correct a Flow Calibration Factor (FCF) based on a stiffness change.

Factors that affect flexural stiffness also affect Coriolis flow meter sensitivity (flow calibration factor). Flexural stiffness is the static spring rate derived from flexing the flow tube with a known force pattern and measuring the flow tube displacement. Any force pattern could be used to measure flexural stiffness, as long as it is invariant. As an example, the flexural stiffness for a clamped beam is as follows:

$$K_{Flex} = \frac{F}{\delta} = \frac{192EI}{L^3} \tag{11}$$

where:
F—Force (N);
E—Young's Modulus (N/m$^2$);
I—Moment of Inertia (m$^4$);
L—Length (m);
$K_{flex}$—flexural stiffness of flow tube.

For a Coriolis flow meter, if flexural stiffness changes, then so must the calibration factor change. Flexural stiffness of a Coriolis flow meter is defined as:

$$K_{flex} = C_P C_G C_S [EI] \tag{12}$$

where:
$C_P$—effect of force pattern on flexural stiffness;
$C_G$—effect of unflexed tube bend geometry on flexural stiffness;
$C_S$—effect of unflexed tube stress on flexural stiffness.

For a straight tube Coriolis flow meter with no pre-stress, the following expressions show the dependence of calibration factor on EI:

$$\dot{m} = C \left[ \frac{EI}{L^3} \right] \Delta T \tag{13}$$

So the flow calibration factor (FCF) for the straight tube is:

$$FCF = C \left[ \frac{EI}{L^3} \right] \tag{14}$$

where C is a constant determined by mode shape and pick-off locations.

Flow tube flexural stiffness can also be determined by estimating points on a tube frequency response function (FRF) at given frequencies. These points are then used to fit a single degree of freedom model to the data and determine the DC (e.g. zero crossing) point on the FRF.

A flow calibration factor can be validated using a multiple frequency estimation process. Multiple frequency estimation begins by identifying constants $m_1$, $c_1$, $k_1$, $\zeta_1$, $\omega_1$, and $A_1$ using any time domain or frequency domain system identification method. A curve fitting procedure is used to fit a rational continuous time transfer function model to the complex frequency response vector H at the set of frequencies in vector W (in radians/second). The number and location (in frequency) of the FRF data points does affect the quality of the fit. A good fit is achieved using as few as 2 frequency response data points. The derived model is of the form:

$$H(s) = \frac{b(1)s^{N_b} + b(2)s^{(N_b-1)} + \ldots + b(N_b+1)}{s^{N_a} + a(2)s^{(N_a-1)} + \ldots + a(N_a+1)} \tag{15}$$

The driver pickoff mobility (velocity) frequency response data is converted to the receptance (displacement) form. The measured mobility frequency response data H must be multiplied by $1/(i\omega)$. The measured mobility drive loop frequency response H should be from drive coil current (proportional to force) to pickoff voltage (proportional to velocity).

Converting the mobility data to receptance data yields H(s) in the form:

$$H(s) = \frac{b(1)}{a(1)s^2 + a(2)s + a(3)} \tag{16}$$

where $a(1)=1$. The modal parameters of interest are extracted from the transfer function model as follows:

$$A_1 = b(1) \tag{17}$$

-continued $$\omega_1 = \sqrt{a(3)}$$

$$\zeta_1 = a(2)/2/\omega_1$$

The physical parameters can then be calculated using the following equations:

$$m_1 = 1/A_1$$

$$c_1 = 2\zeta_1\omega_1/A_1$$

$$k_1 = \omega_1^2/A_1 \quad (18)$$

Once the physical parameters are determined, changes in the flow calibration factor, as well as other parameters (including changes in the mass and length of the flow tube), are determined and corrected.

In an additional capability, the two or more vibrational responses can also be used to detect and differentiate flow meter structure changes, such as erosion, corrosion, and coating of the flow tube. In one such embodiment, the Coriolis flow meter 5 is vibrated at its resonant frequency so as to enable flow meter 5 to measure mass and density. The mass measurement is based on the following equation:

$$\overset{o}{m} = FCF * [\Delta t - \Delta t_0] \quad (19)$$

Where:

$\overset{o}{m}$ is the mass flow rate;
FCF is the flow calibration factor;
$\Delta t$ is the time delay; and
$\Delta t_0$ is the time delay at zero flow.

The FCF term is proportional to the stiffness of the flow meter. Stiffness is the predominate parameter that affects the flow meter's performance. If the stiffness of the flow meter changes, then the meter's FCF will change. A change in the flow meters performance can be caused by corrosion, erosion, and coating, for example.

Equation (19) can be rewritten to reflect the stiffness:

$$\overset{o}{m} = G * (EI) * [\Delta t - \Delta t_0] \quad (20)$$

Where:

G is a geometric constant associated with a particular sensor;
E is Young's Modulus; and
I is the moment of inertia.

The area moment of inertia, I, changes when the meter's flow tube changes. For example, if the tube corrodes reducing the wall thickness, the area moment of inertia is decreased.

In one embodiment, the invention includes a process for detecting and differentiating flow meter structure changes from indicated changes in flow rate. The process starts with the determination of mass flow rate, $\overset{o}{m}$, using multiple modes and the following equation:

$$\begin{pmatrix} m_1^o \\ m_2^o \\ m_n^o \end{pmatrix} = E \begin{pmatrix} G_1 & & \\ & G_2 & \\ & & G_n \end{pmatrix} \begin{pmatrix} I_1 & & \\ & I_2 & \\ & & I_n \end{pmatrix} \begin{pmatrix} \Delta t_1 & & \\ & \Delta t_2 & \\ & & \Delta t_n \end{pmatrix} - \begin{pmatrix} \Delta T_{1o} \\ \Delta t_{2o} \\ \Delta t_{no} \end{pmatrix} \quad (21)$$

When multiple modes are excited, either from flow noise or forced vibration, the vibration of the mode will couple with the mass flow passing through the flow tube, causing a Coriolis response for each mode. The Coriolis response results in an associated $\Delta t$ which is used to calculate a mass flow reading for each mode.

The mass flow reading for each mode is compared. The resulting mass flow rate must be the same for each mode. If the mass flow readings are equal, the comparison generates a "proper operation" signal and the process restarts. The "proper operation" signal can be in the form of a visible or audible signal to a user, for example.

When a deviation occurs between the mass flow rates, which are outside of acceptable limits, an error signal is generated. The error signal can cause various actions to occur. For instance, the error signal may cause the process to be shut down or may signal a visible or audible warning to an operator who then takes appropriate action.

The density measurements of the Coriolis meter 5 are based on the following equation:

$$2\pi f = \frac{2\pi}{\tau} = \sqrt{\frac{k}{m}} \quad (22)$$

Where:

k is the stiffness of an assembly;
m is the mass of the assembly;
f is the frequency of oscillation; and
$\tau$ is the period of oscillation Equation (22) is the solution of the equation of motion for a single degree-of-freedom system. A Coriolis flow meter at zero flow is represented by an expansion of equation (22), yielding:

$$\frac{2\pi}{\tau} = \sqrt{\frac{EIG_p}{\rho_f A_f + \rho_t A_t}} \quad (23)$$

Where:

E is Young's modulus;
I is the cross-sectional moment of inertia;
$G_p$ is a geometric constant;
A is the cross-sectional area;
$\rho$ is the density
f represents the fluid in the flow meter; and
t represents the material of the flow tube(s).

By rearranging terms, equation (23) can be re-written as:

$$\rho_f = C_1 \tau^2 - C_2 \quad (24)$$

Where:

$$C_1 = G_p \frac{EI}{4\pi^2 A_f}, \quad (25)$$

and $$C_2 = \frac{\rho_t A_t}{A_f} \quad (26)$$

The geometric constant, $G_p$, accounts for geometric parameters such as tube length and shape. The constants, $C_1$ and $C_2$, are determined as part of the normal calibration process at zero flow on two different fluids.

In one embodiment, the invention includes a process for detecting and differentiating flow meter structure changes from changes in indicated density. The process starts with the determination of density, ρ, using multiple modes. Multiple modes can be excited either from flow noise or forced vibration.

The density readings for each mode are compared. The resulting density reading must be the same for each mode. If the density readings are equal, the process generates a "proper operation" signal and the process restarts. The "proper operation" signal can be in the form of a visible or audible signal to a user.

When a deviation occurs between the density readings, which are outside of acceptable limits, an error signal is generated. The error signal can cause various actions to occur. For instance, the error signal may cause the process to be shut down or may signal a visible or audible warning to an operator who then takes appropriate action.

The Coriolis flow meter and method according to the invention can be employed according to any of the embodiments in order to provide several advantages, if desired. The invention provides a flow meter that is capable of measuring various flow characteristics. The invention measures the flow characteristics using at least first and second vibration frequencies to excite the flow meter assembly. The invention advantageously operates a Coriolis flow meter to provide additional measurements of dynamic viscosity, kinematic viscosity, and density without compromising the mass flow measurement performance of the flow meter. The invention can additionally provide shear rate, Reynolds number, VOS, and damping factor values. These various flow characteristics advantageously give more detailed and explicit information on the makeup and behavior of the flow medium.

There are numerous applications in virtually all the major industries for a product which simultaneously measures mass flow, density, and viscosity. In one example, the invention can be used for ship fuel oil blending, wherein kerosene is blended with fuel oil to a given kinematic viscosity specification. The resulting blend can be concurrently metered onto a ship. In order to provide a solution to this application, the mass flow rate, the density, and the viscosity measurements are required.

In another example, the invention can be used for lube oil drum filling. Many different lube oils exist, and they are typically manufactured in a single stream and batch filled into drums. During batch filling of drums, the interface between the different lube oil products must be accurately detected in order to prevent contamination. The interface is detected through a change in product viscosity using the viscosity measurement provided by the invention. The mass flow output is used to accurately batch fill the drums using the mass flow rate measurement provided by the invention.

In another example, the invention can be used for receiving high fructose corn syrup (HFCS) solutions, such as HFCS-55, for example. During the receiving of HFCS solutions, each solution will have a specific density (in Brix) and viscosity quality specification. Brix has been defined as a measure of the percentage of solids in a plant juice or alternatively as a measure of percentage of sucrose (sugar). Clearly, having the ability to measure these quality parameters simultaneously with the mass flow rate is a major benefit to the customer.

What is claimed is:

1. A Coriolis flow meter (5) comprising one or more flow conduits (103), at least two pickoff sensors (105, 105') affixed to the one or more flow conduits (103), and a driver (104) configured to vibrate the one or more flow conduits (103), with the Coriolis flow meter (5) being characterized by:

meter electronics (20) coupled to the at least two pickoff sensors (105, 105') and to the driver (104), with the meter electronics (20) being configured to vibrate the one or more flow conduits (103) of the flow meter with a first vibration frequency and in a first out-of-phase bending mode, measure a first vibrational response of the one or more flow conduits (103), with the first vibrational response being generated in response to the first vibration frequency, vibrate the one or more flow conduits (103) with at least a second vibration frequency and in the first out-of-phase bending mode, measure a second vibrational response, with the second vibrational response being generated in response to the second vibration frequency, and determine at least a mass flow rate and a viscosity using the first vibrational response and the second vibrational response.

2. The Coriolis flow meter (5) of claim 1, with the determining further comprising determining a density.

3. The Coriolis flow meter (5) of claim 1, with the determining further comprising determining a shear rate.

4. The Coriolis flow meter (5) of claim 1, with the determining further comprising determining a Reynolds number.

5. The Coriolis flow meter (5) of claim 1, with the determining further comprising determining a velocity of sound (VOS).

6. The Coriolis flow meter (5) of claim 1, with the determining further comprising determining a pressure.

7. The Coriolis flow meter (5) of claim 1, with the viscosity comprising a kinematic viscosity.

8. The Coriolis flow meter (5) of claim 1, with the viscosity comprising a dynamic viscosity.

9. The Coriolis flow meter (5) of claim 1, further comprising jumping between the first vibration frequency and the second vibration frequency.

10. The Coriolis flow meter (5) of claim 1, further comprising substantially simultaneously vibrating the one or more flow conduits (103) with the first vibration frequency and the second vibration frequency.

11. The Coriolis flow meter (5) of claim 1, further comprising sweeping between the first vibration frequency and the second vibration frequency over a predetermined sweep time period.

12. The Coriolis flow meter (5) of claim 1, with the first vibration frequency and the second vibration frequency being substantially equally spaced above and below a fundamental frequency of the one or more flow conduits (103).

13. The Coriolis flow meter (5) of claim 1, with the one or more flow conduits (103) comprising two, substantially U-shaped flow conduits.

14. A method for determining flow characteristics n a Coriolis flow meter, comprising vibrating one or more flow conduits of the flow meter with a first vibration frequency and in a first out-of-phase bending mode and measuring a first vibrational response of the one or more flow conduits, with the first vibrational response being generated in response to the first vibration frequency, with the method being characterized by:

vibrating the one or more flow conduits with at least a second vibration frequency and in the first out-of-phase bending mode;

measuring a second vibrational response, with the second vibrational response being generated in response to the second vibration frequency; and determining at least a mass flow rate and a viscosity of the flow medium using the first vibrational response and the second vibrational response.

15. The method of claim 14, with the determining further comprising determining a density.

16. The method of claim 14, with the determining further comprising determining a shear rate.

17. The method of claim 14, with the determining further comprising determining a Reynolds number.

18. The method of claim 14, with the determining further comprising determining a velocity of sound (VOS).

19. The method of claim 14, with the determining further comprising determining a pressure.

20. The method of claim 14, with the viscosity comprising a kinematic viscosity.

21. The method of claim 14, with the viscosity comprising a dynamic viscosity.

22. The method of claim 14, further comprising jumping between the first vibration frequency and the second vibration frequency.

23. The method of claim 14, further comprising substantially simultaneously vibrating the one or more flow conduits with the first vibration frequency and the second vibration frequency.

24. The method of claim 14, further comprising sweeping between the first vibration frequency and the second vibration frequency over a predetermined sweep time period.

25. The method of claim 14, with the first vibration frequency and the second vibration frequency being substantially equally spaced above and below a fundamental frequency of the one or more flow conduits.

26. A Coriolis flow meter software product for determining flow characteristics in a Coriolis flow meter, comprising a control software on a computer readable medium configured to direct a processing system to vibrate one or more flow conduits of the flow meter with a first vibration frequency and in a first out-of-phase bending mode, measure a first vibrational response of the one or more flow conduits, with the first vibrational response being generated in response to the first vibration frequency, and a storage system that stores the control software, with the software product being characterized by:

the control software being further configured to direct the processing system to vibrate the one or more flow conduits with at least a second vibration frequency and in the first out-of-phase bending mode, measure a second vibrational response, with the second vibrational response being generated in response to the second vibration frequency, and determine at least a mass flow rate and one or more flow characteristics using the first vibrational response and the second vibrational response.

27. The software product of claim 26, with the determining further comprising determining at least a density and a viscosity of the flow medium.

28. The software product of claim 26, with the determining further comprising determining a shear rate.

29. The software product of claim 26, with the determining further comprising determining a Reynolds number.

30. The software product of claim 26, with the determining further comprising determining a velocity of sound (VOS).

31. The software product of claim 26, with the determining thither comprising determining a pressure.

32. The software product of claim 26, with the viscosity comprising a kinematic viscosity.

33. The software product of claim 26, with the viscosity comprising a dynamic viscosity.

34. The software product of claim 26, further comprising jumping between the first vibration frequency and the second vibration frequency.

35. The software product of claim 26, further comprising substantially simultaneously vibrating the one or more flow conduits with the first vibration frequency and the second vibration frequency.

36. The software product of claim 26, further comprising sweeping between the first vibration frequency and the second vibration frequency over a predetermined sweep time period.

37. The software product of claim 26, with the first vibration frequency and the second vibration frequency being substantially equally spaced above and below a fundamental frequency of the one or more flow conduits.

* * * * *

UNITED STATES PATENT AND TRADEMARK OFFICE
CERTIFICATE OF CORRECTION

PATENT NO.        : 7,716,995 B2
APPLICATION NO.   : 11/908385
DATED             : May 18, 2010
INVENTOR(S)       : Andrew T. Patten, Graeme Ralph Duffill and Denis M. Henrot It is certified that error appears in the above-identified patent and that said Letters Patent is hereby corrected as shown below:

Column 16, line 21, replace "thither" with --further--.

Signed and Sealed this
Twenty-second Day of February, 2011

David J. Kappos
*Director of the United States Patent and Trademark Office*